(12) United States Patent
Merkulov et al.

(10) Patent No.: US 7,408,186 B2
(45) Date of Patent: Aug. 5, 2008

(54) CONTROLLED ALIGNMENT CATALYTICALLY GROWN NANOSTRUCTURES

(75) Inventors: Vladimir I. Merkulov, Knoxville, TN (US); Anatoli V. Melechko, Knoxville, TN (US); Michael A. Guillorn, Knoxville, TN (US); Douglas H. Lowndes, Knoxville, TN (US); Michael L. Simpson, Knoxville, TN (US)

(73) Assignee: UT-Battelle LLC, Oak Ridge, TN (US)

( * ) Notice: Subject to any disclaimer, the term of this patent is extended or adjusted under 35 U.S.C. 154(b) by 0 days.

(21) Appl. No.: 11/089,099

(22) Filed: Mar. 24, 2005

(65) Prior Publication Data

US 2005/0167651 A1 Aug. 4, 2005

Related U.S. Application Data

(62) Division of application No. 10/068,795, filed on Feb. 6, 2002, now Pat. No. 6,958,572.

(51) Int. Cl.
*H01L 21/00* (2006.01)

(52) U.S. Cl. .......................... 257/40; 257/17; 977/843; 977/943

(58) Field of Classification Search .................. 257/40, 257/17; 977/843, 943
See application file for complete search history.

(56) References Cited

U.S. PATENT DOCUMENTS

| | | | |
|---|---|---|---|
| 6,183,817 B1 | 2/2001 | Gersonde | |
| 6,447,663 B1 | 9/2002 | Lee et al. | |
| 6,536,106 B1 | 3/2003 | Jackson et al. | |
| 6,630,772 B1 | 10/2003 | Bower et al. | |
| 6,692,568 B2 | 2/2004 | Cuomo et al. | |
| 6,755,956 B2 | 6/2004 | Lee et al. | |

(Continued)

FOREIGN PATENT DOCUMENTS

EP 1 129 990 A1 9/2001

(Continued)

OTHER PUBLICATIONS

Chen et al "Field emission of different oriented carbon nanotubes", Applied Physics Letters, vol. 76, No. 17 (Apr. 24, 2000).*

(Continued)

*Primary Examiner*—Laura M Schillinger
(74) *Attorney, Agent, or Firm*—John Bruckner PC

(57) ABSTRACT

Systems and methods are described for controlled alignment of catalyticaly grown nanostructures in a large-scale synthesis process. A composition includes an elongated nanostructure including a first segment defining a first axis and a second segment coupled to the first segment, the second segment defining a second axis that is substantially nonparallel to the first axis. A method includes: generating an electric field proximate an edge of a protruding section of an electrode, the electric field defining a vector; and forming an elongated nanostructure located at a position on a surface of a substrate, the position on the surface of the substrate proximate the edge of the protruding section of the electrode, at least one tangent to the elongated nanostructure i) substantially parallel to the vector defined by the electric field and ii) substantially nonparallel to a normal defined by the surface of the substrate.

2 Claims, 7 Drawing Sheets

U.S. PATENT DOCUMENTS

| | | | |
|---|---|---|---|
| 6,756,025 B2 * | 6/2004 | Colbert et al. | 423/447.3 |
| 6,756,026 B2 * | 6/2004 | Colbert et al. | 423/447.3 |
| 6,824,755 B2 * | 11/2004 | Colbert et al. | 423/447.1 |
| 6,873,095 B1 * | 3/2005 | Kjellman et al. | 313/336 |
| 6,939,525 B2 * | 9/2005 | Colbert et al. | 423/447.1 |
| 6,958,572 B2 * | 10/2005 | Merkulov et al. | 313/311 |
| 7,029,751 B2 * | 4/2006 | Fan et al. | 428/402 |
| 7,245,068 B2 * | 7/2007 | Merkulov et al. | 313/311 |
| 7,276,266 B1 * | 10/2007 | Khare et al. | 427/533 |
| 2002/0088938 A1 * | 7/2002 | Colbert et al. | 250/306 |
| 2002/0163079 A1 | 11/2002 | Awano | |
| 2003/0148577 A1 * | 8/2003 | Merkulov et al. | 438/238 |
| 2005/0167651 A1 * | 8/2005 | Merkulov et al. | 257/17 |
| 2005/0170553 A1 * | 8/2005 | Merkulov et al. | 438/100 |
| 2005/0191417 A1 * | 9/2005 | Fan et al. | 427/248.1 |
| 2007/0102111 A1 * | 5/2007 | Monsma et al. | 156/296 |
| 2007/0274555 A1 * | 11/2007 | Crowley | 381/399 |
| 2007/0298520 A1 * | 12/2007 | Renaud et al. | 438/3 |
| 2008/0006319 A1 * | 1/2008 | Bettge et al. | 136/244 |
| 2008/0026168 A1 * | 1/2008 | Fan et al. | 428/34.1 |

FOREIGN PATENT DOCUMENTS

| | | | |
|---|---|---|---|
| WO | WO 99/40812 | * | 8/1999 |
| WO | WO 00/09443 | | 2/2000 |

OTHER PUBLICATIONS

Merkulov et al, "Alignment mechanism of carbon nanofibers produced by plasma enhanced chemical vapor deposition", Applied Physics Letters, vol. 79, No. 18, Oct. 29, 2001.*

Bonard et al., Field emission properties of multiwalled carbon nanotubes, Ultramicroscopy 73 (1998) pp. 7-15, 1998.

Xu et al., A method for fabricating large-area, patterned, carbon nanotube field emitters, Applied Physics Letters, vol. 74, No. 17, Apr. 26, 1999, pp. 2549-2551.

Growth and structure of carbon nanotubes produced by thermal chemical vapor deposition, Cheol Jin Lee et al., Carbon 39 (2001) 1891-1896.

Electric-field-directed growth of aligned single-walled carbon nanotubes, Yeugang Zhang et al., Applied Physics Letters vol. 79 No. 19, Nov. 5, 2001.

Collins, et al. "Engineering Carbon Nanotubes and Nanotube Circuits Using Electrical Breakdown" Science, vol. 292, pp. 706-709, Apr. 27, 2001.

Rueckes, et al. "Carbon-Nanotube-Based Nonvolatile Random Access Memory for Molecular Computing" Science, vol. 289, pp. 94-97, Jul. 7, 2000.

Choi, et al. "Fully sealed, high-brightness carbon-nanotube field-emission display", Applied Physics Letters, vol. 75, No. 20, pp. 3129-3131, Nov. 15, 1999.

Steven, et al. "Improved fabrication approach for carbon nanotube probe devices," Applied Physics Letters, vol. 77, No. 21, pp. 3453-3455, Nov. 20, 2000.

Guillorn, "Fabrication of gated cathode structures using an in situ grown vertically aligned carbon nanofiber as a field emission element", Journal of Vacuum Science, pp. 573-578, Mar./Apr. 2001.

Merkulov, et al. "Shaping carbon nanostructures by controlling the synthesis process," Applied Physics Letters, vol. 79, No. 8, pp. 1178-1180, Aug. 20, 2001.

Merkulov, et al. "Patterned growth of individual and multiple vertically aligned carbon nanofibers," Applied Physics Letters, vol. 76, No. 24, pp. 3555-3557, Jun. 12, 2000.

Baker, "Catalytic Growth of Carbon Filaments," Carbon, vol. 27, No. 3, pp. 315-323, Oct. 24, 1988.

Merkulov, et al. "Alignment mechanism of carbon nanofibers produced by plasma-enhanced chemical-vapor deposition," Applied Physics Letters, vol. 79, No. 18, pp. 2970-2972, Oct. 29, 2001.

Ren, et al. "Growth of a single freestanding multiwall carbon nanotube on each nanonickel dot," Applied Physics Letters, vol. 75, No. 8, pp. 1086-1088, Aug. 23, 1999.

Guillorn, et al. "Microfabricated field emission devices using carbon nanofibers as cathode elements", Journal of Vacuum Science Technology B19(6), pp. 2598-2601, Nov./Dec. 2001.

Lee, et al., "Realization of Gated Field Emitters for Electrophotonic Applications Using Carbon Nanotube Line Emitters Directly Grown into Submicrometer Holes," Advanced Materials Communications, vol. 13, No. 7, pp. 479-482, Apr. 4, 2001.

Wang, et al., "Flat panel display prototype using gated carbon nanotube field emitters," Applied Physics Letters, vol. 78, No. 9, pp. 1294-1296, Feb. 26, 2001.

Dean, et al., "The environmental stability of field emission from single-walled carbon nanotubes" Applied Physics Letters, vol. 75, No. 19, pp. 3017-3019, Nov. 8, 1999.

Baylor, et al., "Field emission from isolated individual vertically aligned carbon nanocones" Journal of Applied Physics, vol. 91, No. 7, pp. 4602-4606, Apr. 1, 2002.

Merkulov, et al., "Scanned-probe field-emission studies of vertically aligned carbon nanofibers" Journal of Applied Physics, vol. 89, No. 3, pp. 1933-1937, Feb. 1, 2001.

Xueping, et al., "A method for fabricating large-area, patterned, carbon nanotube field emitters," Applied Physics Letters, vol. 74, No. 17, pp. 2549-2551, Apr. 26, 1999.

Rinzler, et al., "Unraveling Nanotubes: Field Emission from an Atomic Wire" Science, New Series, vol. 269, No. 5230, pp. 1550-1553, May 9, 2002.

Matsumoto, et al., "Ultralow biased field emitter using single-wall carbon nanotube directly grown onto silicon tip by thermal chemical vapor deposition," Applied Physics Letters, vol. 78, No. 4, pp. 539-540, Jan. 22, 2001.

Saito, et al., "Field Emission Patterns from Single-Walled Carbon Nanotubes," Japan Journal Applied Physics, vol. 36, pp. 1340-1342, Oct. 1, 1997.

Guillorn, et al., "Operation of a gated field emitter using an individual carbon nanofiber cathode," Applied Physics Letters, vol. 79, No. 21, pp. 3506-3508, Nov. 19, 2001.

* cited by examiner

WIDE TRENCH

NARROW TRENCH

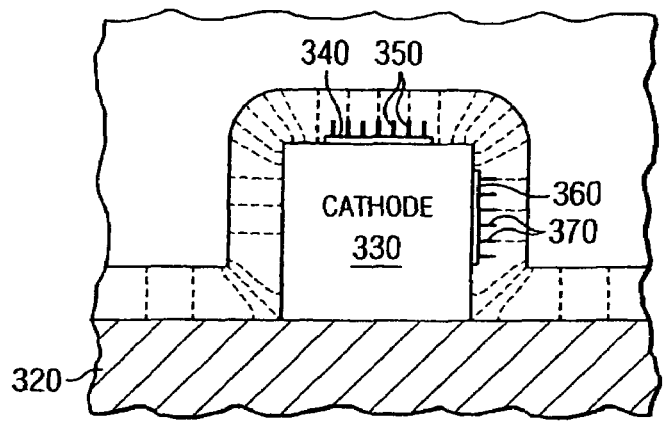
*FIG. 3A*
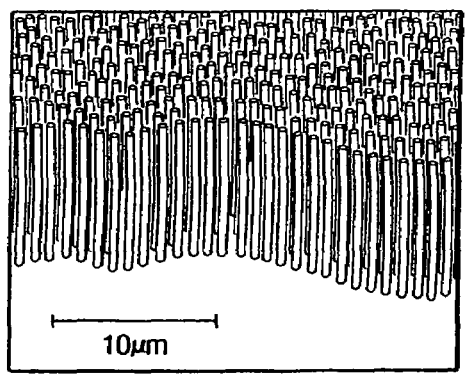  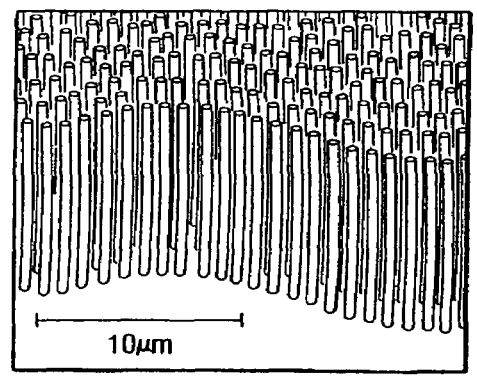
*FIG. 3B*  *FIG. 3C*

FIG. 4A
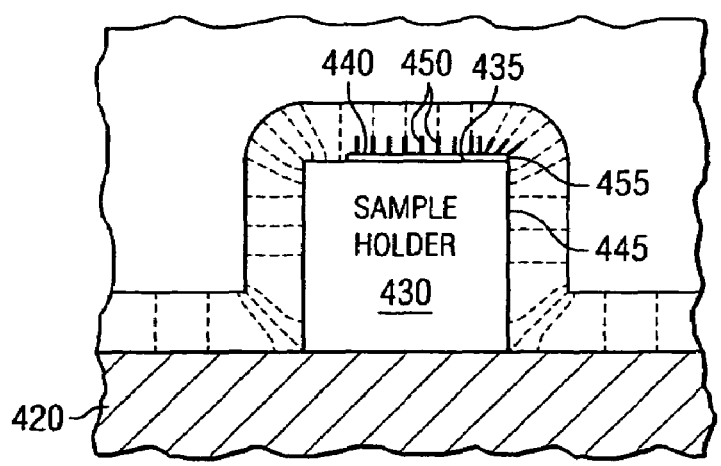
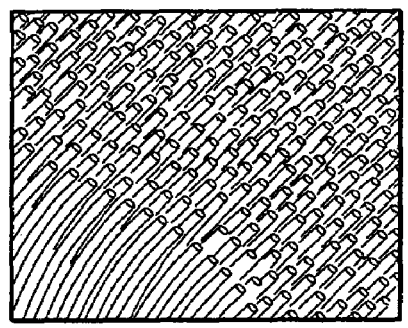
FIG. 4B
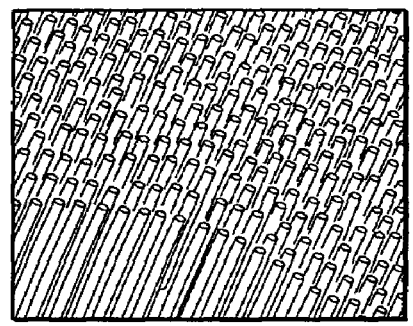
FIG. 4C
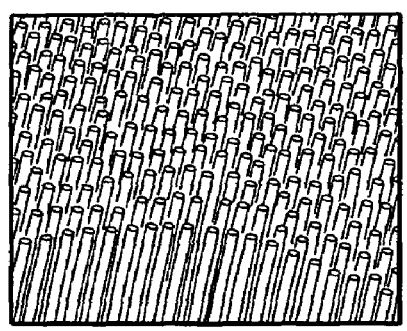
FIG. 4D
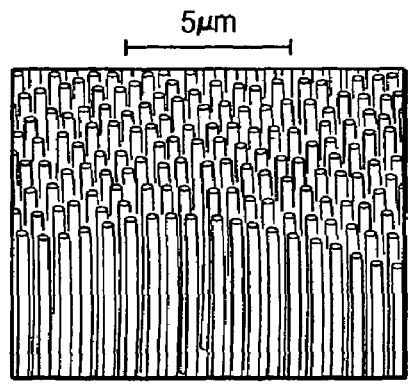
FIG. 4E

CONTROLLED ALIGNMENT CATALYTICALLY GROWN NANOSTRUCTURES

CROSS-REFERENCE TO RELATED APPLICATION

This application is a divisional of, and claims a benefit of priority under 35 U.S.C. 120 from utility patent application U.S. Ser. No. 10/068,795, filed Feb. 6, 2002 now U.S. Pat. No. 6,958,572, the entire contents of which are hereby expressly incorporated herein by reference for all purposes.

STATEMENT AS TO RIGHTS TO INVENTIONS MADE UNDER FEDERALLY-SPONSORED RESEARCH AND DEVELOPMENT

This invention was made with United States Government support under contract to UT-Battelle, L.L.C. The Government has certain rights in this invention.

BACKGROUND OF THE INVENTION

1. Field of the Invention

The invention relates generally to the field of nanotechnology. More particularly, the invention relates to nanostructures that are elongated, methods of making elongated nanostructures and machinery for making such nanostructures.

2. Discussion of the Related Art

The fabrication of commercially valuable devices based upon nanoscale components requires large-scale processes that allow massive production of these components. As a practical matter, such large scale processes need to i) mass produce nanoscale components with well specified properties, (e.g., shape, structure, chemical composition, etc.), ii) enable secure placement of these components in an appropriate orientation that may be dictated by end product functionality, and iii) facilitate attachment of robust input and output (IO) connections.

Elongated nanostructures are exemplified by carbon nanofibers and carbon nanotubes. Carbon nanotubes are a material with superior electronic and mechanical properties. Several research groups have recently demonstrated fabrication of nanoscale devices based upon carbon nanotubes (Collins and Arnold, 2001; Rueckes et al., 2000; Choi et al., 1999; Stevens et al., 2000). Despite vast advances in this field, there remain unsolved problems such as the requirements to (a) synthesize large quantities of CNTs with predetermined properties, (b) place them in a required configuration and (c) create IO connections, all in the context of a fast mass production fabrication process.

The suitability of vertically aligned carbon nanofibers (VACNFs) and vertically aligned carbon nanotubes (VACNTs) for nanoscale device fabrication has been previously demonstrated (Guillom et al., 2001). VACNFs have been deterministically synthesized at predetermined locations using large-scale fabrication processes such as lithography and plasma-enhanced chemical vapor deposition (PECVD). The deterministic VACNF growth that has been achieved includes the control of the location, length, diameter, and shape of VACNFs (Merkulov et al., 2001; Merkulov et al., 2000). The control of the VACNF orientation has generally been limited to the direction perpendicular (normal) to the substrate. What is needed is a mass production technology that can (i) fabricate large quantities of elongated nanostructures with predetermined properties, (ii) place them in a required configuration and (iii) facilitate the creation of IO connections.

Heretofore, the requirements of synthesizing large quantities of elongated nanostructures with well defined properties, arranging them in a desired configuration, and facilitating the creation of input/output connections have not been fully met. What is needed is a solution that simultaneously addresses all of these requirements.

SUMMARY OF THE INVENTION

There is a need for the following embodiments. Of course, the invention is not limited to these embodiments.

According to an aspect of the invention, a method comprises: generating an electric field proximate an edge of a protruding section of an electrode, the electric field defining a vector; and forming an elongated nanostructure located at a position on a surface of a substrate, the position on the surface of the substrate proximate the edge of the protruding section of the electrode, at least one tangent to the elongated nanostructure i) substantially parallel to the vector defined by the electric field and ii) substantially non-parallel to a normal defined by the surface of the substrate. According to another aspect of the invention, a method comprises: generating an electric field proximate a position on a surface of a substrate, the electric field defining a vector; forming an elongated nanostructure located at the position on the surface of the substrate; then changing a direction associated with the vector; and continuing to form the elongated nanostructure, at least one tangent to the elongated nanostructure substantially non-parallel to a normal defined by the surface of the substrate. According to another aspect of the invention, a method comprises: generating an electric field proximate a position on a surface of a substrate, the electric field defining a vector; forming an elongated nanostructure located at the position on the surface of the substrate; then moving the position on the surface of the substrate; and continuing to form the elongated nanostructure, at least one tangent to the elongated nanostructure substantially non-parallel to a normal defined by the surface of the substrate. According to another aspect of the invention, a composition comprises an elongated nanostructure including a first segment defining a first axis and a second segment coupled to the first segment, the second segment defining a second axis that is substantially nonparallel to the first axis. According to another aspect of the invention, an apparatus comprises an electrode including: a protruding section defining an edge; and a nonprotruding section coupled to the protruding section, wherein the edge is adapted to deflect an electric field generated with the electrode and. at least one section selected from the group consisting of the protruding section and the nonprotruding section is adapted to support a substrate for the growth of elongated nanostructures.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals (if they occur in more than one view) designate the same elements. The invention may be better understood by reference to one or more of these drawings in combination with the description presented herein. It should be noted that the features illustrated in the drawings are not necessarily drawn to scale.

FIGS. 3A-3C illustrate views of nanostructures coupled to a cathode, representing embodiments of the invention.

FIGS. 4A-4E illustrate views of angled nanostructures coupled to a cathode, representing embodiments of the invention.

DESCRIPTION OF PREFERRED EMBODIMENTS

The invention and the various features and advantageous details thereof are explained more fully with reference to the nonlimiting embodiments that are illustrated in the accompanying drawings and detailed in the following description. Descriptions of well known starting materials, processing techniques, components and equipment are omitted so as not to unnecessarily obscure the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

Within this application several publications are referenced by author's name and publication year within parentheses. Full citations for these, and other, publications may be found at the end of the specification immediately preceding the claims after the section heading References. The disclosures of all these publications in their entireties are hereby expressly incorporated by reference herein for the purpose of indicating the background of the invention and illustrating the state of the art.

The below-referenced U.S. Patent Applications disclose embodiments that were satisfactory for the purposes for which they are intended. The entire contents of U.S. patent application Ser. No. 09/795,660, filed Feb. 27, 2001, and U.S. patent application Ser. No. 09/810,531, filed Mar. 15, 2001, are hereby expressly incorporated by reference herein for all purposes.

In general, the context of the invention is nanotechnology. The context of the invention can include physics, such as for example scanning probe microscopy. The context of the invention can also include chemistry, such as for example, molecular synthesis.

The invention can include one or more elongated nanostructures having a principal axis that is aligned at a non-normal angle relative to a supporting substrate. The invention can also include one or more elongated nanostructures whose principal axis is deviated. The invention thus relates to elongated nanostructures of the type that can be termed kinked.

The invention can include methods of making the non-normal aligned and/or deviated elongated nanostructures. The invention can also include apparatus for making the non-normal aligned and/or deviated elongated nanostructures.

Figure 1A:
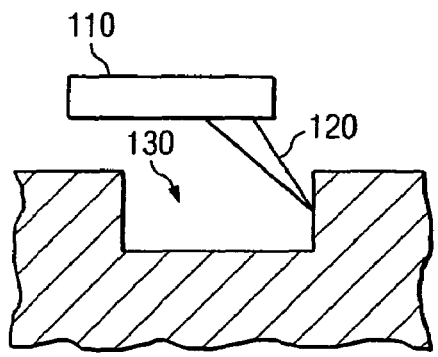
FIGS. 1A and 1B illustrate schematic views of angled and kinked nanostructures, representing embodiments of the invention.
Figure 1B:
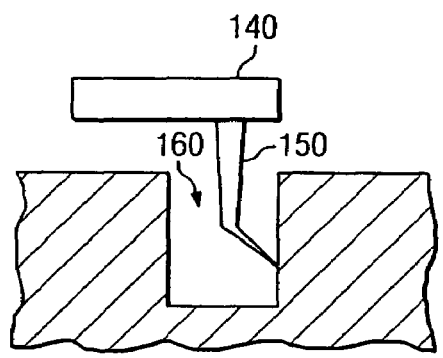

FIGS. 1A and 1B depict a schematic representation of the tip shapes required for inspecting (FIG. 1A) wide and (FIG. 1B) narrow trenches. In FIG. 1A, a cantilever 110 is coupled to an elongated nanostructure 120. The elongated nanostructure 120 is shown contacting a sidewall of a wide trench 130. In FIG. 1B, another cantilever 140 is coupled to a kinked elongated nanostructure 150. The kinked elongated nanostructure 150 is shown contacting a sidewall of a narrow trench 160. The angular deviation of the kinked elongated nanostructure 150 permits the structure to penetrate the narrow trench 160 at a steep angle, thereby enabling sensing of deeply receded features. The kinked elongated nanostructure 150 in FIG. 1B is also suitable for inspecting wide trenches.

The ability to control the orientation of a nanoscale object over a broad range of angles is a very important technological and scientific aspect and can be highly beneficial for production of various nanoscale devices. For instance, fabrication of probes for scanning microscopy in which a cantilever tip is oriented at a relatively large angle to the normal to the cantilever surface could allow inspection of sidewalls of relatively wide trenches (see FIG. 1A), and a kinked tip would allow inspection of narrow trenches (FIG. 1B). The ability to do such inspection can be quite valuable for many applications in various technological fields, in particular for the semiconductor industry. The invention can include a method for synthesis of aligned CNFs, in which the CNF orientation is not fixed to the direction parallel to the substrate normal but can be controlled over a wide range of angles. The alignment control aspect of the invention is not limited to CNFs or CNTs only but can be applied for any other structures whose growth process is similar to the catalytic growth of CNFs/CNTs (Merkulov et al., 2001; Baker, 1989). The invention can also include an apparatus that allows mass production of variably oriented CNFs.

The invention can include a method for controlling the alignment of catalytically grown nanostructures, in particular carbon nanotubes (CNTs) and/or nanofibers (CNFs), in a plasma-enhanced chemical vapor deposition process. The control of alignment can be achieved by positioning the samples in the vicinity of geometrical features of the sample holder, where bending of the electric field lines occurs. The growth of CNFs aligned at various angles to the substrate and kinked CNFs that include two parts aligned at different angles has been demonstrated. In addition, the invention can include a design of an apparatus that allows mass-production of nanostructures aligned at a variable angle to the substrate and of kinked nanostructures with angled tips.

In order to initiate growth of a single CNT or CNF, formation of catalyst nanoparticles may be required (Merkulov et al., 2000). Nickel (Ni) and nickel-iron (Ni—Fe) alloy catalysts can be used. However, other catalysts, such as Fe, Co, etc. can be utilized as well. To form "forests" of chaotically placed CNFs, catalyst thin films were used. For synthesis of individual CNFs, catalyst dots were produced using electron beam lithography and metal evaporation. The catalyst nanoparticles were formed by dc plasma pre-etching of the catalyst thin films with ammonia and annealing them at the elevated temperatures (~700° C.) in a vacuum chamber. Direct-current (dc) plasma-enhanced chemical vapor deposition (PECVD) was used to produce vertically aligned carbon nanostructures. However, other plasma deposition techniques such as RF (radio frequency) or microwave plasma CVD can also be used. A mixture of a carbonaceous gas (e.g., acetylene) and an etchant (e.g., ammonia) was used. The substrates were heated directly by placing them on a heater plate (the cathode of the plasma discharge) and the growth temperature was ~700° C., although higher and lower temperatures can be used.

Figure 2A:
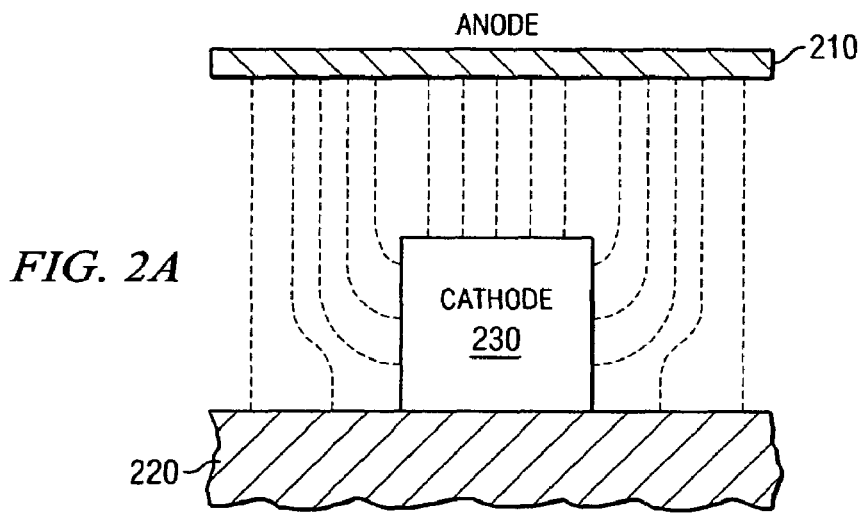
FIGS. 2A and 2B illustrate schematic views of cathode-anode configurations, representing embodiments of the invention.
Figure 2B:
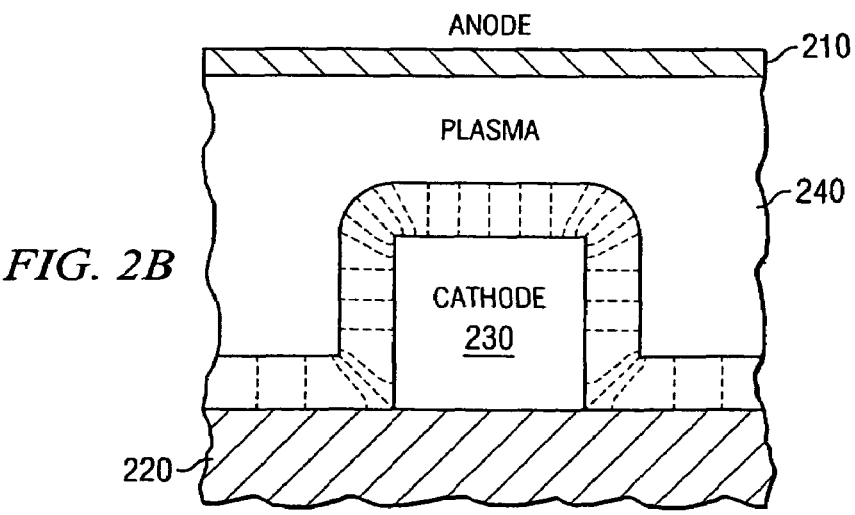

FIGS. 2A and 2B depict a schematic representation of the cathode-anode configuration and the corresponding electric field lines (dotted line) that form in the absence (FIG. 2A) and presence (FIG. 2B) of the plasma. In FIG. 2A an anode 210 is coupled to a cathode 220 that includes a protuberance 230. The protuberance can be termed a sample holder, a substrate or simply one of the electrodes, in this example, the cathode. Further, separate sample holder(s) and/or separate substrate(s) can be coupled to the protuberance. The resulting field lines are demarcated by dashed lines. The electrode and cathode are generically known as electrodes and conventionally demarcated by an applied basis. The invention is not limited to locating the protuberance 230 on the cathode 220 since the invention can include locating the protuberance on the anode.

In FIG. 2B, a plasma 240 has been introduced. Again, the field lines are demarcated by dashed lines. It can be appreciated that the presence of the plasma changes the shape and/or density of the field lines. This change can be termed deflection and the resulting field lines deflected. It is important to appreciate that, although the field line around the entire sidewall of the protuberance are affected, the field lines nearest the edges defined by the protuberance 230 are affected most by the introduction of the plasma 240.

Without being bound by theory, the orientation of CNFs synthesized by PECVD may occur due to the presence of the catalytic nanoparticle at the CNF tip and/or an electric field that is present during the growth process. In the past the field has nominally been directed perpendicular to the substrate surface (Merkulov et al., 2001). In contrast, the invention can include the use of a field that is substantially nonperpendicular to the substrate surface. Without being bound by theory, the direction of the electric field lines may determine the orientation of the elongated nanostructures (e.g., CNFS). Therefore, in order to control the CNF orientation, the direction of the electric field lines may need to be controlled. One way to achieve this control is to control the angle between an anode surface and a cathode surface, given that no physical shielding of the electric field (e.g., plasma) is present between the two electrodes. An example of such an arrangement is shown in FIG. 2A. While the anode is a flat plate, the cathode can have, for example, a three dimensionally extended rectangular shape. As a result, around the top facet of the cathode the electric lines are normal to the surface, whereas around the cathode sidewalls, bending of the electric field lines occurs. Thus, synthesis of CNFs oriented at some angle to the normal is possible. The inventors note that for the field line bending to occur, the cathode does not need to have a rectangular shape, but can have a triangular, trapezoidal, circular, oval, or any other cross section, extended shape. The inventors also note that in the absence of plasma the relative positions and/or functions of the anode and cathode can be reversed. The important point is that the cathode (anode) face at which the catalyst nanoparticle and/or growing top of the structure is located should be oriented at a non-zero angle relative to the anode (cathode) plane.

In contrast to the situation described with reference to FIG. 2A above, during a PECVD process a plasma is present between the two electrodes, as shown in FIG. 2B, the plasma surrounds all faces of the sample holder (nominally in this description the cathode). Consequently, the entire sample holder surface, except for the regions around the edges, is surrounded by electric field lines that are straight and oriented perpendicular to the surface of the cathode. As a result, CNFs located far enough from the edges are aligned perpendicular to the substrate surface, regardless of whether the growth occurs on the top face or the sidewalls of the sample holder (i.e., in this description, the cathode). This is illustrated in FIGS. 3A-3C which show two CNF forests grown on the top and sidewall faces (coupled substrates) of the sample holder.

Referring to FIG. 3A, a first substrate 340 has been located on a protuberance 330 that composes a cathode 320. The first substrate 340 can be removably connected to the protuberance 330. A plurality of elongated nanostructures 350 are coupled to the first substrate 340. The plurality of elongated nanostructures 350 are substantially parallel to a normal to the first substrate 340 since the field lines above the first substrate 340 are substantially parallel to the normal to the first substrate. A second substrate 360 has also been located on the protuberance 330. The second substrate 360 can also be removably connected to the protuberance 330. Another plurality of elongated nanostructures 370 are coupled to the second substrate 360. The another plurality of elongated nanostructures 370 are substantially parallel to a normal to the second substrate 360 since the field lines at the second substrate 360 are substantially parallel to the normal to the first substrate. Since the plane of the second substrate is perpendicular to the plane of the first substrate, the second plurality of elongated nanostructures are perpendicularly orientated with regard to the first plurality of elongated nanostructures.

Together, FIGS. 3A-3C depict a schematic representation of an actual experimental setup during a PECVD process, in which the substrates are located far from the sample holder (nominally the cathode) edges. FIGS. 3B-3C are scanning electron microscopy images showing that the resultant CNFs are substantially vertically aligned, regardless of whether the substrate was placed on top or sidewalls of the sample holder. As will be discussed in more detail below, had the substrates be positioned closer to the edges, the resultant CNFs would not have been substantially vertically aligned. Referring to FIG. 4A, an electrode 420 includes a sample holder 430. A substrate 440 is removably coupled to a surface 435 of the sample holder 430. A plurality of elongated nanostructures 450 are coupled to the substrate 440. The sample holder defines a sample holder edge 445 which is proximate a substrate edge 455 of the substrate 440.

Together, FIGS. 4A-4E depict schematic representation of an actual experimental setup during the PECVD process, in which the substrate is located close to the sample holder edge, (FIG. 4A) and scanning electron microscopy images showing the resultant CNF forests located at (FIG. 4B) 100, (FIG. 4C)

500, (FIG. 4D) 1000, and (FIG. 4E) 2000 µm away from the edge and aligned at ~38, 26, 12, and 5° angles to the substrate normal, respectively.

Far away from the cathode edges the electric field lines are straight and perpendicular to the normal to the cathode surface. However, the direction and shape of the field lines is different around the cathode edges. Significant bending of the electric field lines occurs in that region around the edges. The closer to the edge the nanostructures are grown, the more bending takes place. At the very edge the bending is the largest. As the distance away from the edge increases, the field line bending decreases until the lines become perfectly straight. Thus, it is possible to employ this phenomenon to synthesize CNFs that are aligned at a variable angle to the substrate normal. FIG. 4A shows an experimental set up in which the substrate edge is aligned with that of a sample holder having a rectangular-like shape. In this case, the CNF alignment will deviate the most from the normal to the substrate at the substrate/sample holder edge. As the distance from the edge increases, the alignment becomes closer to the normal until perfectly vertical (perpendicular to the substrate) CNFs (VACNFs) are obtained. As shown in FIG. 4B-E CNFs with variable alignment angle can be synthesized this way and the alignment angle depends on the distance between the CNF location and the substrate/sample holder edge.

The invention can include starting the elongated nanostructure growth process with the substrate in a first position relative to a protuberance edge and/or field line orientation, and then moving the substrate. The growth process can be interrupted during movement of the substrate to create an abrupt change in the shape of the structure, and/or the growth process can be continuous, thereby creating a curved shape. Movement of the substrate can be achieved inside the PECVD vacuum chamber with actuators that are readily commercially available.

Figure 5:
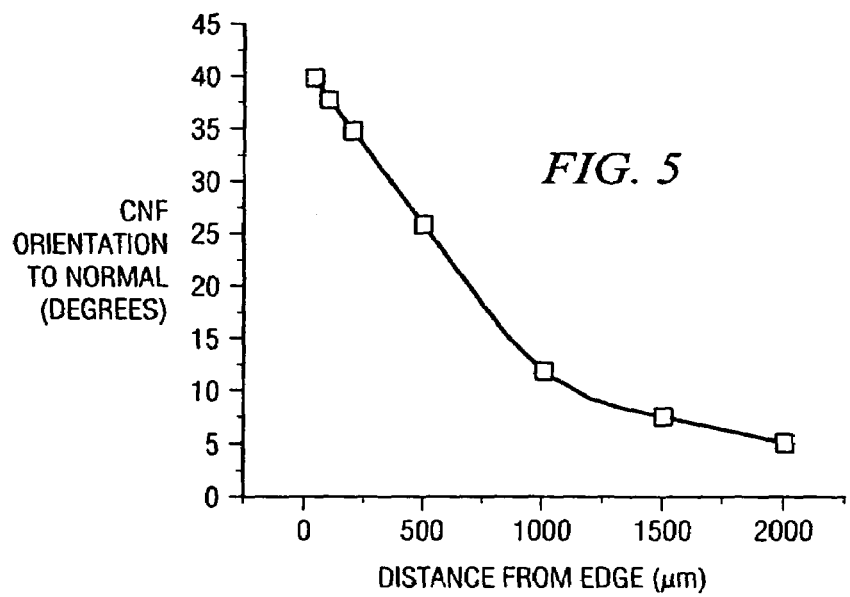
FIG. 5 illustrates a plot of carbon nanofiber orientation to normal versus distance from a cathode edge, representing embodiments of the invention.

FIG. 5 depicts a plot showing the CNF alignment angle to the substrate normal as a function of the distance away from the sample holder edge. The deterministic alignment angle of the VACNF forest as a function of the distance from the edge is shown in FIG. 5. It can be clearly seen that the angle relative to the normal decreases with the distance away from the edge and approaches zero at large distances. The meaning of large being in-part a function of the field strength.

FIGS. 6A-6F depict SEM images, taken at (FIG. 6A) 0 and (FIG. 6B) 45° tilt angles, of an array of individual CNFs grown in the vicinity (~10 µm) of the substrate and the sample holder edge and of single CNFs grown at ~(FIG. 6C) 10, (FIG. 6D) 80, (FIG. 6E) 300, and (FIG. 6F) 580 µm from the edge and aligned at ~42, 30, 15, and 6° to the substrate normal. The images in (FIGS. 6C-6F) were taken at a 45° tilt angle.

Figure 6A:
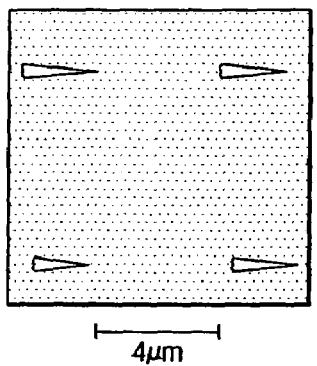
FIGS. 6A-6F illustrate views of nanostructures, representing embodiments of the invention.
Figure 6B:
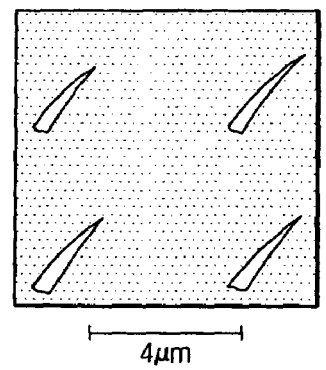
Figure 6C:
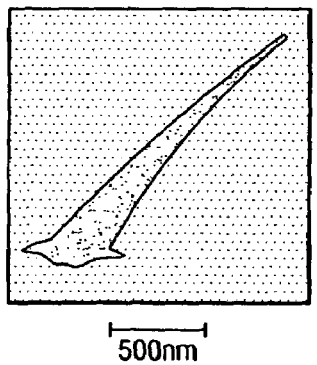
Figure 6D:
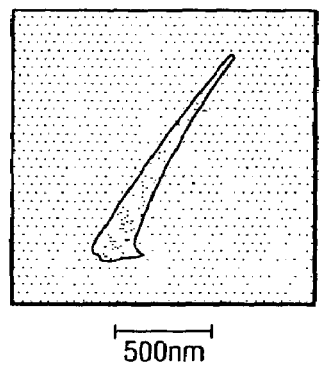
Figure 6E:
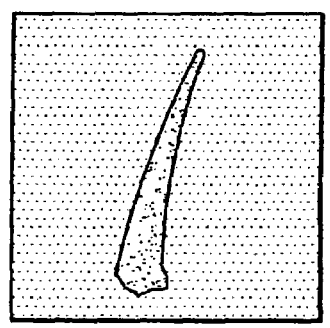
Figure 6F:
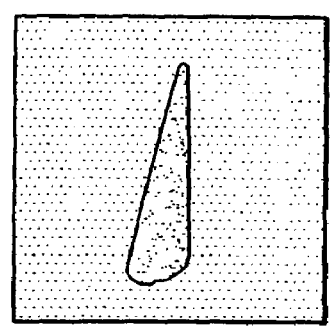

Still referring to FIGS. 6A-6F, the invention makes possible the synthesis of individual CNFs aligned at a variable angle to the substrate normal. To grow individual CNFs, patterned catalyst dots of ~100 nm in diameter were formed. Following this, the sample was positioned on the cathode sample holder so that the catalyst dots were located close to the edge, similar to the arrangement in FIG. 4A. The resultant CNFs, located close to the edge of the substrate/sample holder, are aligned at a relatively large angle to the normal, as shown in FIG. 6A and 6B. Just as in the case of the CNF forests, the alignment angle of individual CNFs also is a function of the distance from the substrate/sample holder edge. This variation can be appreciated from FIG. 6C-F.

Figure 7A:
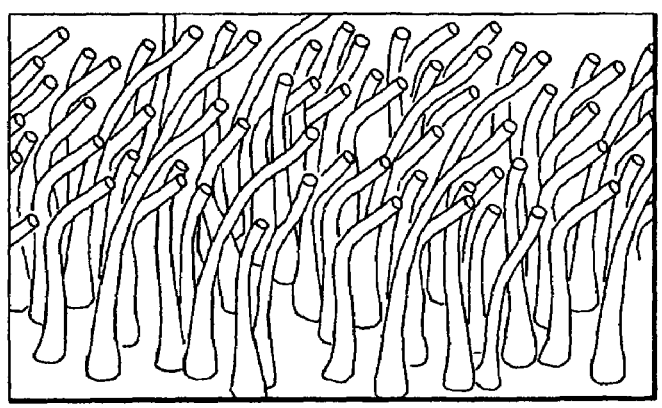
FIGS. 7A-7C illustrate views of kinked nanostructures, representing embodiments of the invention.
Figure 7B:
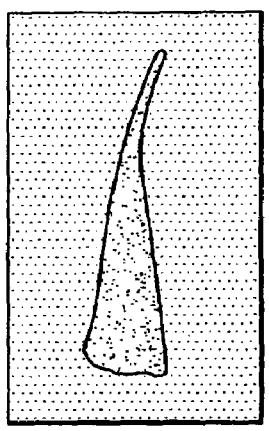
Figure 7C:
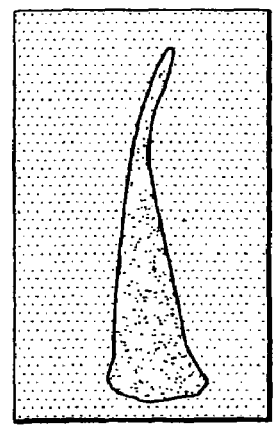

FIGS. 7A-7C depict SEM images of (FIG. 7A) a forest of and (FIGS. 7B-7C) individual kinked CNFs (KCNFs). KCNFs can include two sections: the vertical base and the tip oriented at a non-zero angle to the substrate normal. KCNFs are grown in a two step process: (I) catalyst located far from the sample holder edge (vertical growth direction) and catalyst located close to the sample holder edge (off vertical growth direction).

KCNFs are just one example of a generic class of kinked elongated nanostructures. The kinking process can be applied to carbon nanotubes, as well as to fibers and tubes of other materials. Geometrically, kinked (kinky) elongated nanostructures may be defined as including a first segment defining a first axis and a second segment coupled to the first segment, the second segment defining a second axis that is substantially nonparallel to the first axis.

The ability to control the CNF alignment allows for synthesis of kinked structures such as that shown in FIG. 1B. Such a kinked structure includes two sections: a section that is aligned substantially perpendicular to the substrate and a second section that is aligned at a substantially non-zero angle to the substrate normal. The first section can be synthesized when the catalyst pattern, at which the CNF growth occurs, is located at a large distance from the sample holder edge. In this case, the electric field lines are straight and perpendicular to the substrate surface and vertically aligned CNFs are formed. Following this, the substrate can be repositioned such that the catalyst is located near the sample holder edge. In this repositioned case, bending of the electric field lines occurs at the CNF location and CNFs start to grow off normal. As a result, kinked CNFs (KCNF) such as shown in FIG. 7 can be formed.

Of course, the kinked structure can include more than two sections. Third, fourth or more sections can be located before, between, or after the first and second sections.

Figure 8A:
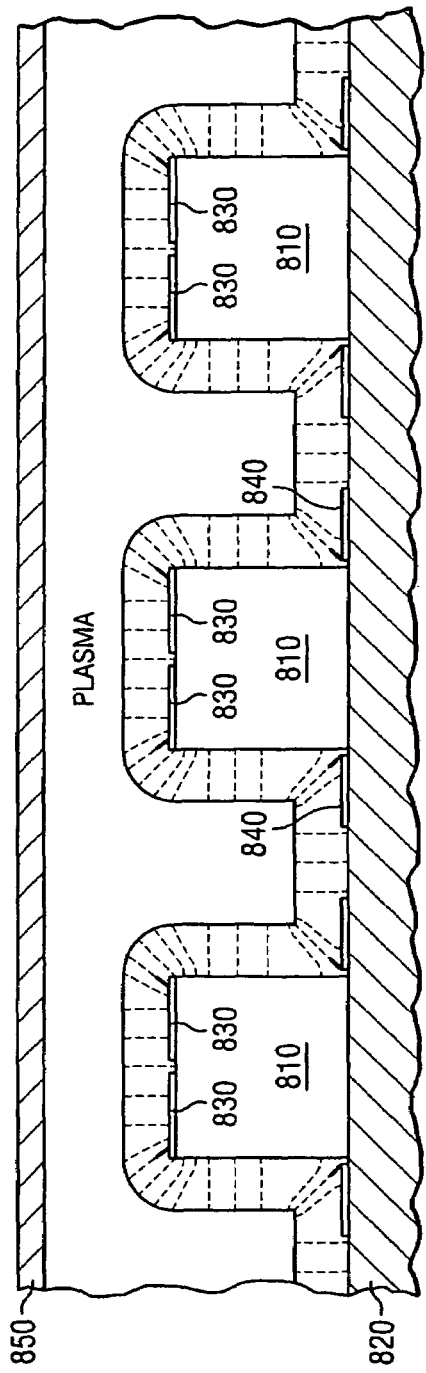
FIGS. 8A-8B illustrate schematic views of a plural cathode-anode configuration, representing an embodiment of the invention.
Figure 8B:
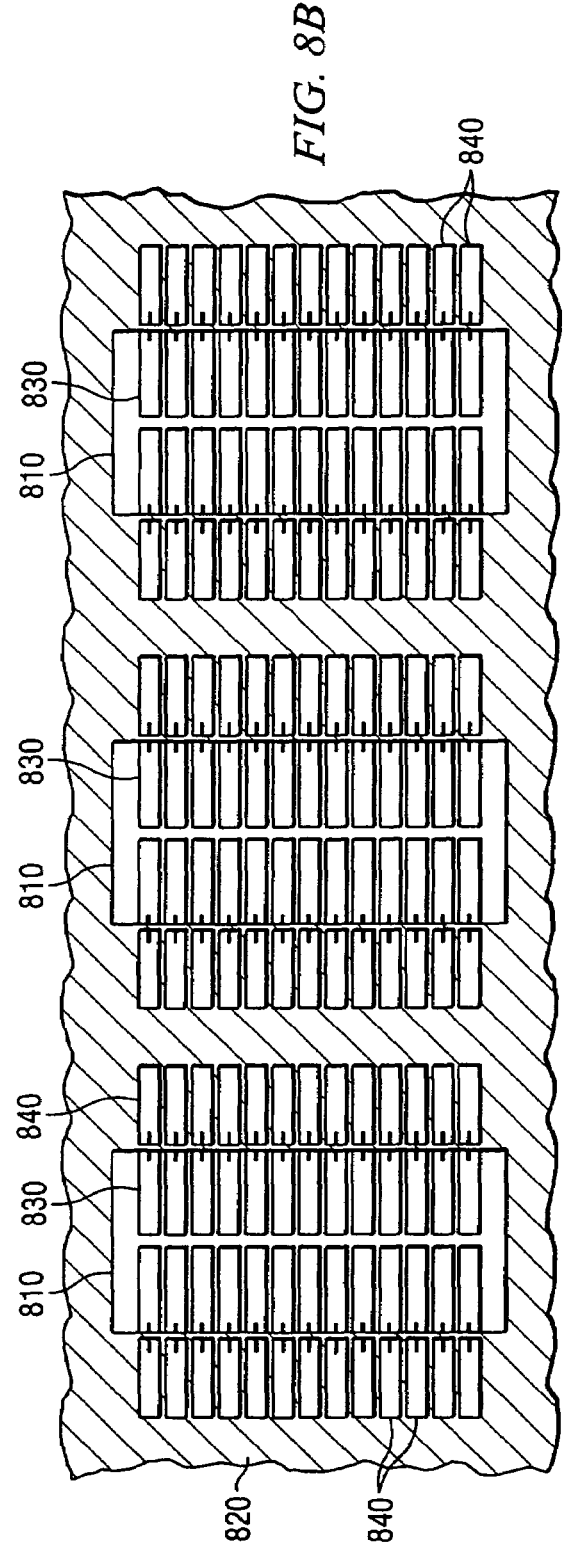

FIGS. 8A-8B depict side (FIG. 8A) and top (FIG. 8B) views of a sample holder arrangement that allows large-scale fabrication of devices based on elongated nanostructures (e.g., CNFs) that are oriented at a non-zero degree to the substrate normal. The substrate holder provides multiple steps at which the electric field line bending occurs and consequently variably aligned CNFs can be produced. At the upper corners of the sample holder, CNFs with alignment pointed outward from the center of the substrate can be produced. In contrast, the lower corners of the sample holder can yield CNFs that are aligned toward the center of the substrate.

Referring to FIG. 8A, an elevational view of a plurality of protuberances 810 coupled to an electrode 820 is depicted. In this embodiment, two upper pluralities of substrates 830 and two lower pluralities of substrates 840 is associated with each of the protuberances 810. A plasma represented by dots is located between the electrode 820 and another electrode 850. It can be appreciated that the field lines cause the elongated nanostructures being grown on the upper pluralities of substrates to tilt away from the centers of the substrates, while the elongated nanostructures being grown on the lower pluralities of substrates tilt in toward the center of the substrates. Thus, the "sign" (inward, outward) of the CNF angle to the normal can be changed by controlling the placement of the substrate on the upper or lower (or intermediate) surfaces of the sample holder. Although in this embodiment all of the protuberances 810 are coupled to a single electrode in a planar arrangement, the protuberances could be coupled to a multiplicity of electrodes and/or arranged in a nonplanar array.

Referring to FIG. 8B, a top view of the apparatus shown in FIG. 8A is depicted. From this view it can be seen that each of the elongated nanostructures is coupled to its own substrate. The substrates can function as input and/or output connections. Thus, the elongated nanostructures can be individually robustly coupled to an I/O connection.

The optimal growth conditions can be different for the upper and lower surfaces. Thus, separate growth runs may be required for the inward and outward aligned CNFs. The alignment angle can be controlled by changing the distance between the CNF location and the sample holder edge: the smaller the distance, the larger the angle. As can be clearly seen from FIGS. 8A and 8B, large-scale deposition, i.e. synthesis of multiple samples in a single growth run, is possible.

Figure 9A:
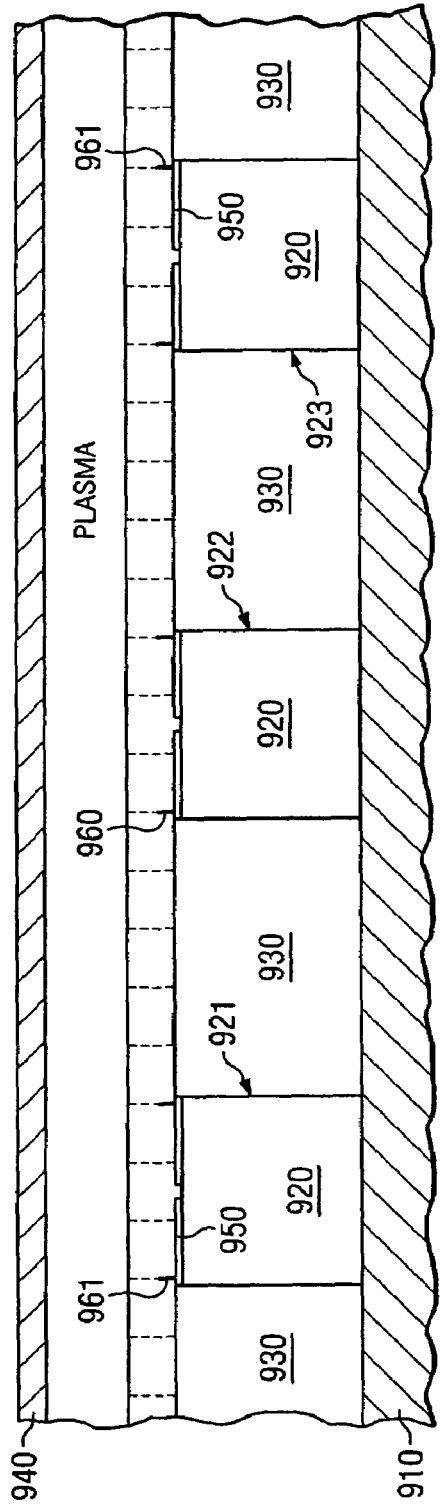
FIGS. 9A-9B illustrate schematic views of a plural cathode-anode configuration that is reconfigurable, representing an embodiment of the invention.
Figure 9B:
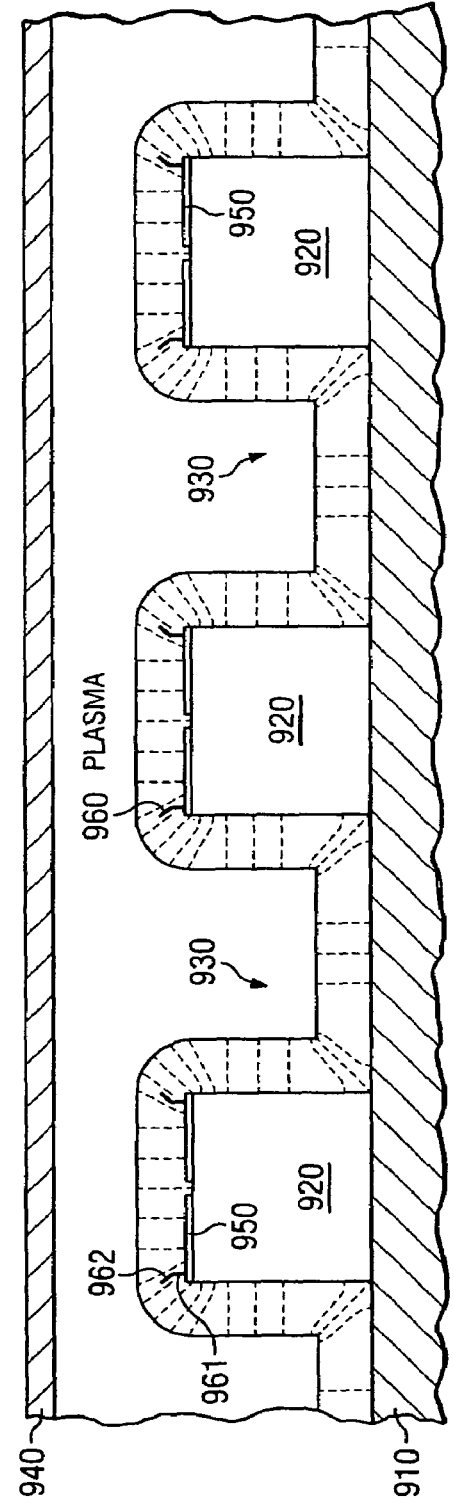

FIGS. 9A-9B depict a schematic representation of a sample holder that allows synthesis of kinked CNFs (KCNFS) without interrupting the growth process. In the "IN" position the movable part of the sample holder creates a flat surface in the sample plane and therefore vertical CNFs are obtained (FIG. 9A). In the "OUT" position, the movable part is moved away so that multiple steps are formed on the sample holder. As a result, bending of the field lines occurs, the CNF growth starts to proceed in an off-vertical direction, and KCNFs are obtained.

Referring to FIG. 9A, an electrode 910 includes a first section 920 and a second section 930. The first section 920 includes three subsections 921, 922, 923. Two pluralities of substrates 950 are shown on each of the subsections 921, 922 and 923. An elongated nanostructure is coupled to each of the substrates 950. The second section 930 is movable and is shown in FIG. 9A in an exposed (in) position. The second section 930 can also include subparts that are optionally independently movable. A plasma represented by dots can be generated between the electrode 910 and a counter electrode 940. In this configuration, the field lines are substantially perpendicular to the plane of the substrates. Therefore, the elongated nanostructure segments 961 grown with the apparatus in this configuration are substantially parallel to the normals to the substrates 950. Referring to FIG. 9B, the second section 930 is shown in a retracted (out) position. In this way, the first section takes on the quality of a protruding section. Alternatively, the second section 930 can be lowered into the body of the electrode 910. In another alternative embodiment, the first section can be raised up from the body of the electrode 910. The first section 920 can be termed a protruding section since it has the capability of extending beyond the second section 930. The second section 930 can be termed a nonprotruding section since it has the capability of being both flush and recessed. In the configuration shown in FIG. 9B, the field line are deflected near the edges 950 defined by the first section 920. The elongated nanostructure segments 962 grown with the apparatus in this configuration are substantially nonparallel to the normals to the substrates 950. The degree of deviation can be controlled by adjusting the relative positions between the first section 920 and the second section 930 and by adjusting the distance between the substrates 950 and the edge of the first section 920.

As noted above, FIGS. 9A and 9B show a possible configuration of a sample holder that allows synthesis of KCNFs without interrupting the growth process. The sample holder includes two parts that can move relative to each other. During the growth of the vertical part of KCNFs, the movable part of the sample holder is moved in (up in FIG. 9a) so that the edges of the two parts coincide (FIG. 9A). This creates a virtually flat continues surface in the substrate plane and consequently vertically aligned CNFs are formed. Following this, the movable part of the substrate holder is moved out (down in FIG. 9B) so that the steps around the substrate edges are created (FIG. 9B). The electric field lines will bend at the step edges that are revealed by moving the movable part out and consequently KCNFs similar to those shown in FIG. 7 will be formed.

The disclosed embodiments show the upper and lower end edges of a three dimensional rectangle as the structure for performing the function of deflecting the electric field from an orientation normal to the substrate, but the structure for deflecting the electric field can be any other structure capable of performing the function of deflecting the field, including, by way of example, a circle, an oval or ellipse, a cube, or pyramid, or any other shape.

While not being limited to any particular performance indicator or diagnostic identifier, preferred embodiments of the invention can be identified one at a time by testing for the presence of non-normal aligned elongated nanostructures. The test for the presence of aligned nanostructures can be carried out without undue experimentation. The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The term approximately, as used herein, is defined as at least close to a given value (e.g., preferably within 10% of, more preferably within 1% of, and most preferably within 0.1% of). The term substantially, as used herein, is defined as largely but not necessarily wholly that which is specified. The term generally, as used herein, is defined as at least approaching a given state (e.g., preferably within 10% of, more preferably within 1% of, and most preferably within 0.1% of). The term deploying, as used herein, is defined as designing, building, shipping, installing and/or operating. The term means, as used herein, is defined as hardware, firmware, and/or software for achieving a result. The term program or phrase computer program, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer system.

Practical Applications of the Invention

A practical application of the invention that has value within the technological arts is atomic force microscopy (AFM), scanning tunneling microscopy (STM), and other scanning probe microcopies. The invention is useful in conjunction with nanoelectronics. The invention is useful in conjunction with biological probes. Further, the invention is useful in conjunction with any other techniques where nanostructures aligned at a variable angle to the substrate can be utilized. There are virtually innumerable uses for the invention, all of which need not be detailed here.

Advantages of the Invention

The invention, can be cost effective and advantageous for at least the following reasons. The invention allows the fabrication of nanostructures aligned at a (continuously) variable angle to the substrate, not just vertically aligned nanostructures. The invention allows the fabrication of "kinked" nanostructures that consist of several sections that all can be aligned at different angles to the substrate. The invention improves quality and/or reduces costs compared to previous approaches.

All the disclosed embodiments of the invention disclosed herein can be made and used without undue experimentation in light of the disclosure. The invention is not limited by theoretical statements recited herein. Although the best mode of carrying out the invention contemplated by the inventor(s) is disclosed, practice of the invention is not limited thereto. Accordingly, it will be appreciated by those skilled in the art that the invention may be practiced otherwise than as specifically described herein.

Fabrication of nanostructures other than CNFs or CNTs. The only requirement is that the growth process of these nanostructures should be similar to the catalytic growth of CNFs/CNTs. Different sample holder shape can be used. Different catalyst can be used. Different gasses can be used.

Further, the individual components need not be formed in the disclosed shapes, or combined in the disclosed configurations, but could be provided in virtually any shapes, and/or combined in virtually any configuration. Further, the individual components need not be fabricated from the disclosed materials, but could be fabricated from virtually any suitable materials. Further, variation may be made in the steps or in the sequence of steps composing methods described herein. Further, although the electrode described herein can be a separate module, it will be manifest that the electrode may be integrated into the system with which it is associated. Furthermore, all the disclosed elements and features of each disclosed embodiment can be combined with, or substituted for, the disclosed elements and features of every other disclosed embodiment except where such elements or features are mutually exclusive.

It will be manifest that various substitutions, modifications, additions and/or rearrangements of the features of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements.

The appended claims are not to be interpreted as including means-plus-finction limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

REFERENCES

Collins, Arnold, Avouris, *Science,* 292:706, 2001.
Rueckes, Kim, Joselevich, Tseng, Cheung, Lieber, *Science,* 289:94, 2000.
Choi, Chung, Kang, Kim, Jin, Han, Lee, Jung, Lee, Park, Kim, *Appl. Phys. Lett.,* 75:3129, 1999.
Stevens, Nguyen, Cassell, Delzeit, Meyyappan, Han, *Appl. Phys. Lett.,* 77:3453, 2000.
Guillorn, Simpson, Bordonaro, Merkulov, Baylor, Lowndes, *Vac. Sci. Techol.,* B19:573, 2001.
Merkulov, Guillorn, Lowndes, Simpson, Voelkl, *Appl. Phys. Lett.,* 79:1178, 2001.
Merkulov, Lowndes, Wei, Eres, Voelkl, *Appl. Phys. Lett.,* 76:3555, 2000.
Chen, Shaw, Guo, *Appl. Phys. Lett.,* 76:2469, 2000.
Baker, *Carbon,* 27:315, 1989.
Merkulov, Melechko, Guillorn, Lowndes, Simpson, *Appl. Phys. Lett.,* 79:2970, 2001.
Ren, Huang, Wang, Wen, Xu, Wang, Calvet, Chen, Klemic, Reed, *Appl. Phys. Lett.,* 75:1086, 1999.

What is claimed is:

1. A composition, comprising an elongated nanostructure including a first elongated segment defining a first axis and a second elongated segment coupled to the first segment, the second elongated segment defining a second axis that is substantially nonparallel to the first axis;
a substrate coupled to the elongated nanostructure;
another elongated nanostructure coupled to the substrate; and
wherein the elongated segments are substantially linear.

2. The composition of claim 1, wherein the another elongated nanostructure defines another axis that is substantially parallel to one axis selected from the group consisting of the first axis and the second axis.

* * * * *